US006403536B1

(12) United States Patent
Forsythe et al.

(10) Patent No.: US 6,403,536 B1
(45) Date of Patent: Jun. 11, 2002

(54) COMPOSITION AND METHOD FOR REDUCING ODOR OF SUBSTITUTED NAPHTHALENES

(76) Inventors: Darol Forsythe, 15401 Cartwright Rd., Boise, ID (US) 83703; John M. Forsythe, 4277 Balivi La., Nampa, ID (US) 83687

( * ) Notice: Subject to any disclaimer, the term of this patent is extended or adjusted under 35 U.S.C. 154(b) by 0 days.

(21) Appl. No.: 09/573,329

(22) Filed: May 18, 2000

(51) Int. Cl.$^7$ ..................... A01N 27/00; A01N 65/00; A01N 37/10; A01N 35/04; A61L 9/01
(52) U.S. Cl. ................. 504/357; 504/118; 504/358; 514/544; 514/699; 514/763; 514/765; 514/974; 424/736; 424/747; 424/765; 424/769; 424/770; 424/774; 424/775; 424/76.8; 424/76.9
(58) Field of Search ................. 514/763, 544, 514/974, 699, 765; 424/195.1, 736, 747, 765, 769, 770, 774, 775, 76.8, 76.9; 504/118, 357, 358

(56) References Cited

U.S. PATENT DOCUMENTS

| 5,260,260 A | 11/1993 | Gednalske et al. | .......... 504/206 |
| 5,463,180 A | 10/1995 | Gednalske et al. | .......... 504/323 |
| 5,719,102 A | 2/1998 | Gednalske et al. | .......... 504/116 |

FOREIGN PATENT DOCUMENTS

| WO | 98/53678 | * 12/1998 | |

OTHER PUBLICATIONS

The Merck Index, Merck & Co., Inc., Rahway (NJ), 10th edition, p. 5991, 1993.*
Chemical Abstracts 121:3310, abstracting JP 6–107505 (1994).*
WPIDS (Derwent) Abstract, accession No. 1987–069074 (1987).*
Chemical Abstracts 42:7546d–h, abstracting IN 35306 (1947).*
Kirk–Othmer Encyclopedia of Chemical Technology, 4th ed., John Wiley & Sons, New York, 1991, vol. 1, pp. 809–811, 824–825.*
Kirk–Othmer Encyclopedia of Chemical Technology, 4th ed., John Wiley & Sons, New York, 1996, vol. 17, pp. 594–603.*
Chemical Abstracts 61:9350h–9351a–b, "Analysis of some essential oils by gas–liquid partition chromatography" (1964).*
The Chemical Formulary, vol. IV, Chemical Publishing Company of New York, Inc., New York, 1939, p. 41.*

* cited by examiner

Primary Examiner—John Pak
(74) Attorney, Agent, or Firm—TraskBritt

(57) ABSTRACT

A chemical composition and method useful in the treatment of stored potatoes is disclosed. The chemical composition includes a mixture of a substituted naphthalene compound and an odor-neutralizing ingredient. The instant invention also discloses a method for reducing the odor of naturally-occurring or applied substituted naphthalenes. The odor-neutralizing ingredient neutralizes the odor associated with substituted naphthalene compounds.

14 Claims, No Drawings

COMPOSITION AND METHOD FOR REDUCING ODOR OF SUBSTITUTED NAPHTHALENES

BACKGROUND OF THE INVENTION

1. Field of the Invention

The instant invention relates to a composition and method for treating potatoes and, in particular, a composition and method involving substituted naphthalene compounds and odor-neutralizing ingredients, wherein the substituted naphthalenes may be used to treat potatoes during storage while the odor-neutralizing ingredients neutralize the odor associated with the substituted naphthalene compounds. The invention further relates to compositions and methods for neutralizing the odor associated with substituted naphthalene compounds that are either applied to tubers or naturally occurring in tubers.

2. Background of Related Art

Potatoes are harvested by being dug out of the ground. Commercially harvested potatoes are stored in facilities maintained at cool temperatures, typically between 40–45° F., for up to one year before reaching the consumer. As is well known, potatoes begin sprouting if they are not used quickly after harvesting. Untreated potatoes stored at room temperature can begin sprouting within one month of storage. Since commercially harvested potatoes are typically stored for at least 6 to 8 months, sprouting is a very likely occurrence. Even at cool temperatures, untreated potatoes can begin sprouting after a few months of storage. If the harvest becomes entangled with sprouts, the economic value of the whole harvest can be destroyed.

To reduce or prevent sprouting during storage and transportation, potatoes are sprayed with sprout inhibitors. Well known sprout inhibitors include chloroisopropyl-N-carbamate ("CIPC") and substituted naphthalene compounds. Dimethylnaphthalene ("DMN") and its related isomers, such as 1,4 dimethylnaphthalene ("1,4-DMN") or 1,6 dimethylnaphthalene ("1,6-DMN"), are substituted naphthalene compounds known to be effective sprout inhibitors. DMN and its isomers may be preferred over CIPC because DMN does not delay any natural healing processes of the potato, is a naturally occurring component of potatoes, and is non-toxic to humans.

DMN and its isomers are liquid at room temperature and are immiscible in water. A solution, suspension, or emulsion of DMN can be prepared by adding the odor-neutralizing ingredients to 95–99.9% DMN. The solution, suspension, or emulsion can be applied after the potatoes are harvested, typically within 48 hours of harvesting. The solution, suspension, or emulsion may also be sprayed onto the potatoes during transport or the early stages of storage. DMN can also be applied to stored potatoes as a mist or vapor. In addition, the potatoes can be treated by immersion in a DMN bath.

One disadvantage of applying DMN and its isomers as a sprout inhibitor is the objectionable odor of these substituted naphthalene compounds. The odor can be quite noticeable with treated potatoes, especially in storage facilities and during transportation. The odor may even be noticeable with untreated potatoes because DMN is a naturally occurring component of potatoes and is released by the potatoes. The objectionable odor may linger until the product is delivered to a grocer or is ultimately bought by a consumer.

Other patents have addressed the problem of reducing odors of various compounds. In U.S. Pat. No. 5,260,260, issued to Gednalske et al., an ionic surfactant blend containing acidulated soybean soapstock and an emulsifier is disclosed. U.S. Pat. No. 5,463,180, issued to Gednalske et al., discloses a nonionic surfactant blend that reduces the odor of 2,4-dichlorophenoxy acetic acid, a herbicide. The nonionic surfactant blend contains effective quantities of acidulated soybean soapstock and nonoxynol. In U.S. Pat. No. 5,719,102, which is a continuation in part of U.S. Pat. No. 5,463,180, also issued to Gednalske et al., a nonionic surfactant blend is disclosed that reduces the odor of additional herbicides. The nonionic surfactant blend disclosed in the patents issued to Gednalske et al. contains effective quantities of acidulated soybean soapstock and a nonionic surfactant such as nonoxynol. In addition, a method of applying the reduced odor herbicide is disclosed.

SUMMARY OF THE INVENTION

The instant invention includes a composition containing a substituted naphthalene compound in combination with odor-neutralizing ingredients which neutralize the odor associated with the substituted naphthalene compound. The substituted naphthalene compounds suitable for use with the present invention include DMN and its isomers, preferably 1,4-DMN. The odor-neutralizing ingredients suitable for use with the present invention include d-limonene, wintergreen, mint oil, citron, peppermint, vanillin, rose alder, and combinations thereof. In addition to wintergreen, any other mint oil can be used.

The instant invention also comprises a method for reducing the odor associated with substituted naphthalene compounds. The odor-neutralizing ingredients are added to DMN in effective amounts to neutralize the DMN odor. The odor-neutralizing ingredients may be present in amounts from between 0.1 to 3% by volume and are preferably soluble in DMN. In addition, the odor-neutralizing ingredients may be used singly.

Since certain substituted naphthalene compounds are present naturally in potatoes, the distinctive odor in potato storage facilities may be due to naturally occurring DMN or DMN that has been applied to prevent sprout inhibition. Therefore, it may be difficult for a storage manager or treatment applicator to determine whether the odor in a storage facility is due to naturally evolving or applied DMN. The instant invention also comprises the use of odor-neutralizing ingredients in applied DMN solutions, suspensions, or emulsions to enable a storage manager or treatment applicator to easily determine whether DMN has been applied to that storage facility.

In another embodiment of the present invention, a composition containing odor-neutralizing ingredients is applied to potatoes which have either been treated with a substituted naphthalene or which contain naturally occurring substituted naphthalenes (e.g. DMN) in order to neutralize the odor associated with the substituted naphthalene. The odor-neutralizing ingredients suitable for use with the present invention include d-limonene, wintergreen, mint oil, citron, peppermint, vanillin, rose alder, and combinations thereof. In addition to wintergreen, any other mint oil can be used.

DETAILED DESCRIPTION OF THE INVENTION

The present invention relates to the composition and method for neutralizing the odor of sprout inhibitors, specifically substituted naphthalenes such as DMN and its isomers. For example, DMN (more specifically 1,4-DMN) is applied to potatoes during storage and transportation to prevent and reduce sprouting. However, DMN has an objectionable odor that can linger during storage and transportation.

The present invention involves a chemical composition that neutralizes the odor associated with substituted naphthalenes, such as DMN and its isomers. In one embodiment of the invention, the chemical composition is comprised of DMN and odor-neutralizing ingredients in a concentration range effective to neutralize the DMN's odor. Small amounts of odor-neutralizing ingredients, such as d-limonene and wintergreen, are added to effectively neutralize the DMN's odor. The odor-neutralizing ingredients are present in amounts from between 0.1–1% by volume and are preferably soluble in DMN. The odor-neutralizing ingredients may be used alone or in combination.

The present invention also involves a method of reducing odor associated with DMN and its isomers. Odor-neutralizing ingredients, such as wintergreen and d-limonene, are added to DMN in effective amounts to neutralize DMN's odor. For example, it has been found that a DMN solution containing 1% wintergreen and 0.5% d-limonene neutralizes the DMN odor and leaves a faint smell of wintergreen. Higher concentrations of wintergreen also neutralize DMN's odor, however they leave a strong, medicinal smell. It has been observed that lower concentrations of wintergreen than d-limonene neutralize DMN's odor while leaving only a faint smell of the odor-neutralizing ingredient. For instance, a solution containing 1% d-limonene with 0.5% wintergreen neutralizes DMN's odor but leaves a more noticeable d-limonene smell, as compared to the faint wintergreen odor at the same concentration.

In another embodiment, the odor-neutralizing ingredients or composition can be applied to potatoes which have either been treated with a substituted naphthalene or which contain naturally occurring substituted naphthalenes in order to neutralize the odor associated with the substituted naphthalene.

DMN is a liquid at room temperature and is immiscible in $H_2O$. The instant composition can be prepared as a solution, suspension, or emulsion by adding the odor-neutralizing ingredients to 95–99.9% DMN. D-limonene and wintergreen are also insoluble in H2O. Both odor-neutralizing ingredients are colorless liquids at room temperature. D-limonene has a more pleasing smell than wintergreen because wintergreen can produce a medicinal smell at high concentrations. However, lower concentrations of wintergreen can be used to neutralize the DMN smell, leaving only a faint odor of wintergreen.

The resulting odor-neutralizing composition can be applied to the potatoes in any manner, such as is disclosed above. For instance, the composition can be applied as a concentrated or dilute solution, suspension, or emulsion. The composition can be applied in spray, mist, or vapor form. In addition, DMN can be applied by immersing the potatoes in a bath containing the odor-neutralizing composition.

The composition includes odor-neutralizing ingredients such as d-limonene, wintergreen, mint oil, citron, peppermint, vanillin, and rose alder. In addition to wintergreen, any other mint oil can be used. The odor-neutralizing ingredients may be used singly or in combinations thereof.

In a preferred embodiment, the odor-neutralizing ingredients are present in effective amounts to neutralize the odor of DMN. The odor-neutralizing ingredients may be present singly or in combination.

In a more preferred embodiment, the odor-neutralizing ingredients are present in effective amounts from between 0.1–1% by volume in 95–99.9% DMN. The odor-neutralizing ingredients may be present singly or in combination.

In a most preferred embodiment, 1% wintergreen and 0.5% d-limonene by volume are present in 98.6% DMN. At these concentrations, the resulting composition has a faint smell of wintergreen while the DMN odor is neutralized.

EXAMPLE 1

A solution of DMN, 1% wintergreen, and 0.5% d-limonene was prepared. The resulting solution had a pleasant odor. The solution was applied to an object and periodically checked for odor. The odor of DMN on the object was neutralized while a faint odor of wintergreen was detectable.

EXAMPLE 2

A solution of DMN, 1% d-limonene, and 0.5% wintergreen was prepared. The resulting solution had a pleasant odor. The solution was applied to an object and periodically checked for odor. The odor of DMN on the object was neutralized, leaving a detectable odor of d-limonene.

EXAMPLE 3

A solution of DMN, 1% wintergreen, and 0.3% d-limonene was prepared. The DMN odor of the solution was neutralized. The solution was applied to an object and periodically checked for odor. The odor of DMN on the object was neutralized and no noticeable odor from the odor-neutralizing ingredients was detected.

EXAMPLE 4

A solution of DMN, 1% d-limonene, and 0.3% wintergreen was prepared. The DMN odor of the solution was neutralized at these concentrations. The solution was applied to an object and periodically checked for odor. The odor of DMN on the object was neutralized and no noticeable odor from the odor-neutralizing ingredients was detected.

EXAMPLE 5

A solution of DMN, 0.33% wintergreen, and 0.67% d-limonene was prepared. The odor of DMN was neutralized and faint odors of the wintergreen and d-limonene were observed. However, when the solution was later checked for odor, the DMN odor was noticeable and no smell of d-limonene was noticeable.

EXAMPLE 6

A solution of DMN, 0.67% wintergreen, and 0.33% d-limonene was prepared. The odor of the DMN was neutralized in the resulting solution, but the odor of the wintergreen was too strong. When the solution was later checked for odor, the DMN odor was noticeable but no smell of wintergreen was noticeable.

EXAMPLE 7

A solution of DMN and 0.3% wintergreen and 0.3% d-limonene was prepared. The odor of the DMN was neutralized and the odors of the wintergreen and d-limonene were not too strong. However, the DMN smell was noticeable when the solution was later checked for odor. When the solution was applied to an object and periodically checked for odor, the DMN odor was noticeable.

EXAMPLE 8

An object was treated with a solution of DMN, 0.67% wintergreen, and 0.33% d-limonene. When the object was periodically checked for odor, a faint odor of DMN was observed.

EXAMPLE 9

An object was treated with a solution of DMN, 0.33% wintergreen, and 0.67% d-limonene. When the object was periodically checked for odor, a faint smell of d-limonene was observed, suggesting that d-limonene may be less volatile than wintergreen.

EXAMPLE 10

A solution of DMN, 1% mint oil, and 0.5% citron is prepared. The resulting solution has a pleasant odor. The solution is applied to an object and periodically checked for odor. The odor of DMN on the object is neutralized while a faint odor of mint oil is detectable.

EXAMPLE 11

A solution of DMN, 1% mint oil, and 0.5% rose adder is prepared. The resulting solution has a pleasant odor. The solution is applied to an object and periodically checked for odor. The odor of DMN on the object is neutralized while a faint odor of mint oil is detectable.

EXAMPLE 12

A solution of DMN, 1% mint oil, and 0.5% vanillin is prepared. The resulting solution has a pleasant odor. The solution is applied to an object and periodically checked for odor. The odor of DMN on the object is neutralized while a faint odor of mint oil is detectable.

Although specific examples demonstrating the present invention have been described, it is to be understood that the invention defined by the appended claims is not to be limited by the particular details set forth in the above description. One of ordinary skill in the art would understand that many apparent variations are possible without departing from the scope of the appended claims. For example, varying the number of odor-neutralizing ingredients in combination would be understood to be within the scope of the appended claims. In addition, varying the identity of the odor-neutralizing ingredients would be understood to be within the scope of the appended claims.

What is claimed is:

1. A chemical composition comprising a substituted naphthalene and an effective amount of at least one odor-neutralizing ingredient selected from the group consisting of d-limonene, wintergreen, mint oil, citron, peppermint, vanillin, and rose alder.

2. The composition of claim 1, wherein said substituted naphthalene is an isomer of dimethylnaphthalene.

3. The composition of claim 2, wherein said isomer is 1,4-dimethylnaphthalene.

4. A chemical composition comprising an isomer of dimethylnaphthalene and an effective amount of at least one odor-neutralizing ingredient having an effective amount of wintergreen and d-limonene in combination.

5. The composition of claim 4, wherein said effective amount of wintergreen and d-limonene in combination is 1% wintergreen by volume and 0.5% d-limonene by volume.

6. A method for neutralizing the odor of a sprout inhibitor comprising:

providing an effective amount of at least one odor-neutralizing ingredient selected from the group consisting of d-limonene, wintergreen, mint oil, citron, peppermint, vanillin, and rose adder to neutralize the odor associated with a substituted naphthalene; and mixing said effective amount of at least one odor-neutralizing ingredient with said substituted naphthalene.

7. The method of claim 6, wherein said substituted naphthalene is an isomer of dimethylnaphthalene.

8. The method of claim 7, wherein said isomer is 1,4-dimethylnaphthalene.

9. The method of claim 6, wherein said effective amount of at least one odor-neutralizing ingredient is between about 0.3 and 3% by volume.

10. The method of claim 6, wherein said at least one odor-neutralizing ingredient includes an effective amount of wintergreen and d-limonene in combination.

11. The method of claim 10, wherein said effective amount of wintergreen and d-limonene in combination is 1% wintergreen by volume and 0.5% d-limonene by volume.

12. A method for neutralizing the odor of a sprout inhibitor comprising:

providing an effective amount of at least one odor-neutralizing ingredient to neutralize the odor associated with dimethylnaphthalene, wherein said at least one odor-neutralizing ingredient is selected from the group consisting of d-limonene and wintergreen; and mixing said effective amount of at least one odor-neutralizing ingredient with dimethylnaphthalene.

13. A chemical composition comprising an effective quantity of at least one odor-neutralizing ingredient to neutralize the odor associated with dimethylnaphthalene, wherein said at least one odor-neutralizing ingredient includes an effective amount of wintergreen and d-limonene in combination.

14. The composition of claim 13, wherein said effective amount of wintergreen is 1% and d-limonene is 0.5% by volume.

* * * * *